(12) United States Patent
Hsieh

(10) Patent No.: US 10,969,354 B1
(45) Date of Patent: *Apr. 6, 2021

(54) METHOD OF ANALYZING AN ENVIRONMENTAL SAMPLE

(71) Applicant: Florida A&M University, Tallahassee, FL (US)

(72) Inventor: Yuch Ping Hsieh, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/860,860

(22) Filed: Apr. 28, 2020

Related U.S. Application Data

(63) Continuation of application No. 15/843,839, filed on Dec. 15, 2017, now Pat. No. 10,690,605.

(60) Provisional application No. 62/434,672, filed on Dec. 15, 2016.

(51) Int. Cl.
*G01J 5/00* (2006.01)
*G01N 25/08* (2006.01)
*G01N 33/28* (2006.01)

(52) U.S. Cl.
CPC ............ *G01N 25/08* (2013.01); *G01N 33/287* (2013.01); *G01N 33/2823* (2013.01); *F23G 2202/60* (2013.01); *G01J 5/00* (2013.01)

(58) Field of Classification Search
CPC .... G01J 2005/0081; G01J 5/00; G01N 25/72; G01N 30/30; G01N 15/1463; G01N 21/35; G01N 30/78; G01N 31/005; G01K 13/00; C10B 53/00; C10G 1/02; C10G 9/00; C10L 1/02; F23G 2202/60

USPC ......................................................... 436/147
See application file for complete search history.

(56) References Cited

U.S. PATENT DOCUMENTS

| | | | | |
|---|---|---|---|---|
| 3,574,549 A | * | 4/1971 | Eggertsen | G01N 7/14 436/157 |
| 2009/0026362 A1 | * | 1/2009 | Arii | H01J 49/147 250/281 |
| 2010/0116027 A1 | * | 5/2010 | Heggs | G01N 21/766 73/31.04 |
| 2011/0076198 A1 | * | 3/2011 | Bettmann | G01N 33/1846 422/78 |
| 2014/0256054 A1 | * | 9/2014 | Smeets | F23C 3/00 436/160 |
| 2016/0061804 A1 | * | 3/2016 | Chanbasha | G01N 33/287 73/61.61 |
| 2018/0059009 A1 | * | 3/2018 | Kagawa | G01N 1/24 |

FOREIGN PATENT DOCUMENTS

DE 102005014705 A1 * 10/2006 ........... G01N 31/005

* cited by examiner

*Primary Examiner* — Gail Kaplan Verbitsky
(74) *Attorney, Agent, or Firm* — Smith & Hopen, P.A; Steven M. Forte

(57) ABSTRACT

A method of directly analyzing an environmental sample, such as a crude oil sample, to determine distillation ranges, identify elements therein, and/or identify impurities. The method includes performing multi-element scanning thermal analysis (MESTA) on the environmental sample to obtain a thermogram of the elements within the environmental sample, wherein peak information within the thermogram indicates the presence of the elements, compounds, and/or impurities within the particular environmental sample.

19 Claims, 15 Drawing Sheets

TABLES

FIG. 8

Table 1.

| Model Compound | Chemical Formula | MW (g/mole) | Chemical Structure |
|---|---|---|---|
| Single peaks | | | |
| 2-acetyl-5-chlorothiophene | $C_6H_5ClOS$ | 160.5 | 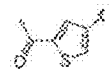 |
| 2-chlorothioxanthen-9-one | $C_{13}H_7ClOS$ | 246.5 | 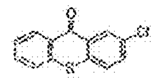 |
| 4-amino-2,1,3-benzothiadiazole | $C_6H_5N_3S$ | 151.0 | 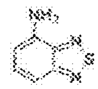 |
| 4,4-diphenyl-tetrathiafulvalene | $C_{18}H_{12}S_4$ | 356.0 | 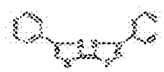 |
| Bathophenanthrolinedisulfonic acid | $C_{24}H_{20}N_2Na_2O_6S_2$ | 590.0 | 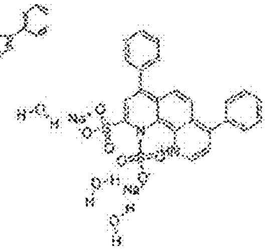 |
| Butadiene sulfone | $C_4H_6O_2S$ | 118.0 | 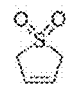 |
| Cystine | $C_6H_{12}N_2O_4S_2$ | 240.3 | 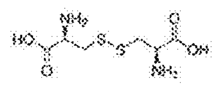 |
| ES | $S_8$ | 256 | |
| Sulfanilamide | $C_6H_8N_2O_2S$ | 172.2 | 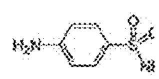 |
| Thiourea | $CH_4N_2S$ | 76.1 | 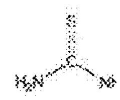 |
| Multiple peaks | | | |
| Bis(diethyldithiocarbamato)dioxo molybdenum (VI) | $C_{10}H_{20}MoN_2O_2S_4$ | 424.5 | 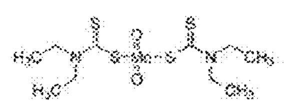 |
| Cysteine | $C_3H_7NO_2S$ | 121.2 | 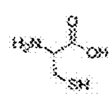 |
| Dithiouracil | $C_4H_4N_2S_2$ | 144.2 | 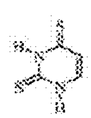 |
| DL-Methionine sulfoxide | $C_5H_{11}NO_3S$ | 165.0 | 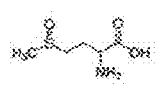 |
| Sodium sulfite | $Na_2SO_3$ | 126.0 | 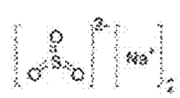 |
| Sulfanilic acid | $C_6H_7NO_3S$ | 173.2 | 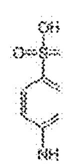 |

| Skewed peaks | | |
|---|---|---|
| Iron (II) sulfide | FeS | 87.8 |
| Pyrite | $FeS_2$ | 119.8 |
| Silver sulfide | $Ag_2S$ | 247.8 |

FIG. 8 (continued)

METHOD OF ANALYZING AN ENVIRONMENTAL SAMPLE

CROSS-REFERENCE TO RELATED APPLICATIONS

This nonprovisional application is a continuation of and claims priority to U.S. Non-Provisional application Ser. No. 15/843,839, entitled "Method of Crude Oil Analysis," filed Dec. 15, 2017 by the same inventor, which claims priority to U.S. Provisional Patent Application No. 62/434,672, entitled "Method of Crude Oil Analysis", filed Dec. 15, 2016, the entirety of which is incorporated herein by reference.

BACKGROUND OF THE INVENTION

1. Field of the Invention

This invention relates, generally, to the analysis of environmental samples. More specifically, it relates to multi-element scanning thermal analysis and uses thereof for crude oil analysis.

2. Brief Description of the Prior Art

Sulfur is an essential element for all organisms. Sulfur also plays an important role in many biogeochemical cycles of terrestrial and aquatic systems on a global scale. Sulfur exists in many oxidative states (from −2 to +6) and forms. Due to the complexity of sulfur forms, many methods have been developed for sulfur analysis over the years, most of them for inorganic sulfur species (Blanchar, R W. *Sulfur in Agriculture*, Tabatabai, M. A., Ed., American Society of Agronomy, Inc./Crop Science Society of America, Inc./Soil Science Society of America, Inc: Madison, 1986, pp 455-490).

Analysis of organic sulfur in solid complex and heterogeneous environmental samples, however, is still difficult. Bulk organic sulfur analyses in those samples are mostly done indirectly. i.e., by the difference between the total and the inorganic sulfur contents. Indirect methods are not only tedious, but they also accumulate the errors of two samplings and two analytical procedures and thus significantly increase the uncertainty of the results. Sophisticated direct methods, such as the combination of solid-state NMR, X-ray photoelectron spectroscopy (XPS) and sulfur X-ray absorption near edge structure (S-XANES), have been applied to the determination of organic sulfur species in a complex matrix of coals (Kelemen, R et al., *Energy & Fuels* 2007, 21, 1548-1561). However, these sophisticated methods are tedious and unavailable to most routine analytical protocols.

Due to the analytical limitations found in the conventional art, along with the lack of a convenient direct analytical method, knowledge pertaining to organic sulfur in solid and heterogeneous environmental samples (e.g., soils, aerosols, coals, and sediments) is poor and very limited. Often, there is an interest in analyzing sulfur in crude oil samples. Detailed crude oil analytical information is required by oil producers, traders, transporters, and refiners. The average quality of crude oil being processed in refineries is becoming higher in sulfur and heavier (Swain, E., 2005. U.S. Refiners Continue to Process Crudes with Lower Gravity, Higher Sulfur. Oil Gas J., Jan. 3, 2005, p. 51-55.), i.e., a greater content of heavy ends or residuum. With the growing demand for transportation fuels, the refiner is faced with mounting pressure to make better use of the "bottom of the barrel"—the residuum that formerly went into low-quality products such as bunker fuel oils. However, as environmental restrictions increasingly limit sulfur and aromatics in transportation and burner fuel oils, refiners are facing new challenges to economically producing a marketable slate of products from heavier, higher sulfur feedstocks. These challenges generally require new or expanded processing and treatment technology at the refinery. This, in turn, demands analytical methods that are fast and convenient to provide necessary information for evaluating feedstock and product quality.

Currently, the primary manner of analyzing crude oil is boiling-point distillation methods plus subsequent sulfur/nitrogen analyses performed in each distillation range. Analytical information on the distillation ranges and their sulfur and nitrogen impurities in crude oils are critically important to almost all sectors of the petroleum industry-including producers, traders, transporters, and refineries. Boiling point distribution provides insight into the composition of crude oil. It is a good estimation of the quantity of products likely to be yielded in refinery processes. These boiling point data are also used to evaluate new crudes, to determine crude quality, and to provide essential information for optimization of refinery processes. Historically, these boiling point data have been obtained by a physical or true boiling point distillation, a lengthy and tedious process that requires a relatively large volume of sample. For instance, standard boiling-point distillation analytical procedures (ASTM D2892-15 and ASTM D5236-13) takes 3-5 days to complete plus additional time for sulfur and nitrogen analyses in each distilled fraction.

Information on sulfur and nitrogen compounds in each distillation range is also critically important to refineries. These sulfur and nitrogen compounds cause corrosion of refinery equipment and the poisoning of catalysts and contribute to environmental pollution, if not removed from the products. Sulfur and nitrogen compounds are determined in each range after the distillation process. The usual turnaround time for distillation and sulfur/nitrogen analyses would be 10 to 20 days and the average charge between $3,000 and $8,000 per sample. In addition, a 50-100% surcharge may be applied for faster service. Further, conventional analytical methods are also "fixed-fraction" operations, meaning that if one wants to know a different option of ranges, one needs to do another analysis from scratch. Conventional methods also produce hazardous materials in a laboratory and cannot be performed on-site.

Alternatively, simulated distillation using GC methods (e.g., ASTM methods D2887, D5307, and D7169) has also been used to rapidly determine the distillation fractions without the need for a conventional physical distillation. However, those ASTM methods have limitations in crude oil test applications. For instance, methods D2887 and D5307 restricted to petroleum products and ranges up to 538° C., and material boiling above 538° C. is reported as residue. ASTM D7169 extends the boiling range distribution through a temperature of 720° C. The amount of residue (or sample recovery) is determined using an external standard. The extended range of this test method is important to the refinery engineer because the data provide refiners the ability to quickly evaluate crude oils and to select those with economic advantages and more favorable refining margins (Villalanti, D. C., Raia, J. C., and Maynard, J. B., 2000. High-Temperature Simulated Distillation Applications in Petroleum Characterization, Encyclopedia of Analytical Chemistry, R. A. Meyers, Ed., John Wiley, Chichester, United Kingdom, Vol. 8, pp. 6726-6741). Moreover, these GC simulation methods do not provide the critical sulfur/ nitrogen information in each distillation range. They are primarily used only for preliminary screening purposes because boiling-point distillation is still needed. Those gas chromatographic simulation methods are usually plagued by the column clogging problems and often show data variation that exceeds the requirements of a crude oil client.

Additionally, on-site and rapid field analyses of crude oils is in big demand in small land oil operators. There are thousands of oil wells actively operating in Kansas, with daily production of an individual well from a few barrels to 300 barrels. NCRA (National Cooperative Refinery Association, personal contact) purchases 90,000 barrels of crude oils from over 700 operators each day. Those crude oils may greatly differ in qualities but were mixed only based on their API gravities and total S contents. There are still some unknowns that may be critical to the subsequent refining processes. A rapid, mobile, and economical crude oil analysis is needed to greatly improve the efficiency and performance of the petroleum industry by providing detail and essential analytical information of crude oils in the market, which is not currently available due to cost and time constraints.

Multi-Element Scanning Thermal Analysis (MESTA)

MESTA is a kinetic, non-equilibrium heating process, in which the deviation of the true peak temperatures of a thermogram is a function of the sample heating rate and the activation energy of the thermal decomposition. MESTA reveals the thermochemical stability of the compounds in a sample, in terms of its C, N and S contents, by thermally scanning the sample from ambient temperature (0° C. or 32° C., if refrigerated) to 800° C. (1,472° F.) under a given atmosphere of carrier gas.

It is suitable for routine analysis of a wide range of solid, liquid, and mixed environmental samples, such as aerosols, soils, sediments, and other environmental samples. MESTA has been proven to be a highly sensitive, quantitative, and reproducible analytical tool. Examples of the use of MESTA are discussed in Y. P. Hsieh et al., Analysis of black carbon in sediments and soils using multi-element scanning thermal analysis (MESTA), Organic Geochemistry 39 (2008) 1562-1571; Hsieh, Y. P., et al. 2010. Chemical signature of biomass burning-emitted PM2.5 and the detection of its presence in the air by a rapid method. Pages 73-78 in K. M. Robertson, K. E. M. Galley, and R. E. Masters (eds.). Proceedings of the 24th Tall Timbers Fire Ecology Conference: The Future of Prescribed Fire: Public Awareness, Health, and Safety. Tall Timbers Research Station. Tallahassee, Fla., USA; Y. P. Hsieh, A novel multi-elemental scanning thermal analysis (MESTA) method for the identification and characterization of solid substances, J AOAC Int. 2007 January-February, 90(1): 54-59; Oindrila Das, et al. Chemical and carbon isotopic characteristics of ash and smoke derived from burning of $C_3$ and $C_4$ grasses, Organic Geochemistry, Volume 41, Issue 3, March 2010, Pages 263-269; Hsieh, Y. P. 2012. New Tools for an old problem. International Innovation/Environment, April issue.: 75-77; Hsieh, Y. P., et al, 2013, Multi-Element Scanning Thermal Analysis (MESTA) of Aerosols and Nano-Carbon Particles. European Aerosol Conference, 2013; and Hsieh, Y. P., et al, 2016. Examination of two assumptions commonly used to determine PM2.5 emission factors for wildfires. Atmospheric Environment 147:274-283. Results have shown that MESTA is a sensitive, quantitative, and reproducible analytical tool.

Table I compares MESTA to a few GC simulation methods.

TABLE 1

Comparison of MESTA and some ASTM GC simulation methods for crude oil boiling point measurement.

| Method | Boiling Range | Element Analyses |
|---|---|---|
| ASTM D2887 | Up to 538° C. | No |
| ASTM D5307 | Up to 538° C. | No |
| ASTM D7169 | Up to 720° C. | No |
| ASTM D6352 | 174° C. to 700° C. | No |
| MESTA | Ambient temp. to 800° C. | C, N, S, H |

Despite the advantages of MESTA, it is unknown how MESTA technology can be used to analyze crude oil due to crude oil analysis requiring special analytical procedures such as sample handling, the composition of the carrier gas and kinetic-effect correction function to match the batch equilibrium condition of the traditional boiling-point distillation method. Accordingly, what is needed is a convenient and versatile organic sulfur analytical method that can be routinely applied to a wide range of and size environmental samples, such as crude oil samples. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions: or is known to be relevant to an attempt to solve any problem with which this specification is concerned.

BRIEF SUMMARY OF THE INVENTION

The long-standing but heretofore unfulfilled need for an improved method of analyzing an environmental sample, such as a crude oil is now met by a new, useful, and nonobvious invention.

It is an object of the current invention to provide a rapid environmental sample analysis based on MESTA technology, where the analysis can obtain the boiling-point distillation ranges plus their respective sulfur/nitrogen impurity information in each range of the environmental sample. In an embodiment, the method can be utilized as a quick (30 minutes), versatile (in a laboratory or on-site mobile service), environmentally friendly (no hazardous waste), and economical (300-$800) method for analyzing a crude oil sample.

In an embodiment, the current invention is a method of directly analyzing an environmental sample to determine distillation ranges simultaneously and sulfur impurities therein, comprising performing multi-element scanning thermal analysis on the environmental sample to obtain a thermogram (e.g., sensitive to less than about 0.01 μg) of one or more elements within the environmental sample, wherein the elements may include sulfur species (e.g., organic sulfur and reduced inorganic sulfur). Optionally, before or during analysis, the temperature of the sample can be calibrated using internal standards of elemental sulfur and silver sulfide. Upon analysis, peak information within the thermogram indicates the presence of the sulfur species within the environmental sample.

Nitrogen impurities in the sample may also be determined simultaneously with the distillation ranges and the sulfur impurities in the sample by performing the multi-element scanning thermal analysis on the sample.

With the sulfur species, the elements may further include a carbon species, a nitrogen species, and a hydrogen species. The sulfur species, carbon species, nitrogen species, and hydrogen species correspond to the distillation properties of hydrocarbon compounds, sulfur compounds, and nitrogen compounds in the environmental sample. Further, differences in ratios of the carbon species, nitrogen species, and sulfur species within the sample can be determined as well.

In an embodiment, the thermal analysis includes continuous scanning in a temperature range from ambient to about 700° C., where the thermograms obtained contains all possible distillation range information. In another embodiment, the thermal analysis includes continuous scanning in a temperature range from about 40° C. to about 700° C. within a programmed sample compartment furnace.

In yet another embodiment, the thermal analysis may include a constant heating rate (e.g., 50° C./min) with the flow of a carrier gas. The carrier gas can be an approximate 40/60 volume mixture of oxygen and helium or pure helium gas. The flow rate of the carrier gas in a sample compartment furnace and a combustion furnace may be about 80 mL/min and about 350 mL/min, respectively. When the elements include sulfur, carbon, nitrogen, and hydrogen, the carrier gas can carry volatile from the sample during heating into the combustion furnace that is fed by pure oxygen, such that the carbon species oxidizes into carbon dioxide, the nitrogen species oxidizes into nitrogen dioxide, the sulfur species oxidizes into sulfur dioxide, and hydrogen oxidizes into water. In this case, the carbon dioxide is quantified by a carbon dioxide infrared analyzer, the nitrogen dioxide is quantified by a nitrogen dioxide chemiluminescent detector, and the sulfur dioxide is quantified by a sulfur dioxide chemiluminescent detector, and an IR analyzer quantifies the water vapor. A multi-channel data logger may then be utilized to record real-time sample temperature, signals from the carbon dioxide, signals from the nitrogen dioxide, signals from water vapor, and signals from the sulfur dioxide. Based on these signals and data, the calibration curves of the carbon species, the nitrogen species, hydrogen species, and the sulfur species can be generated by mixtures of pure cystine and glucose standards.

The area under the peaks may then be normalized within the calibration curves in order to quantify the C, N. H, and S elements.

Optionally, a characteristic carbon thermogram may be obtained to further aid in the identification of compounds within the sample.

In a separate embodiment, the current invention is a method of analyzing a crude oil sample directly to simultaneously determine distillation ranges, sulfur impurities, and nitrogen impurities therein. The method includes any one or more-or even all—of the foregoing steps, characteristics, and benefits.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 8 is a table depicting peak information, including compound, chemical formula, molecular weight, and chemical structure.

DETAILED DESCRIPTION OF THE INVENTION

Figure 1:
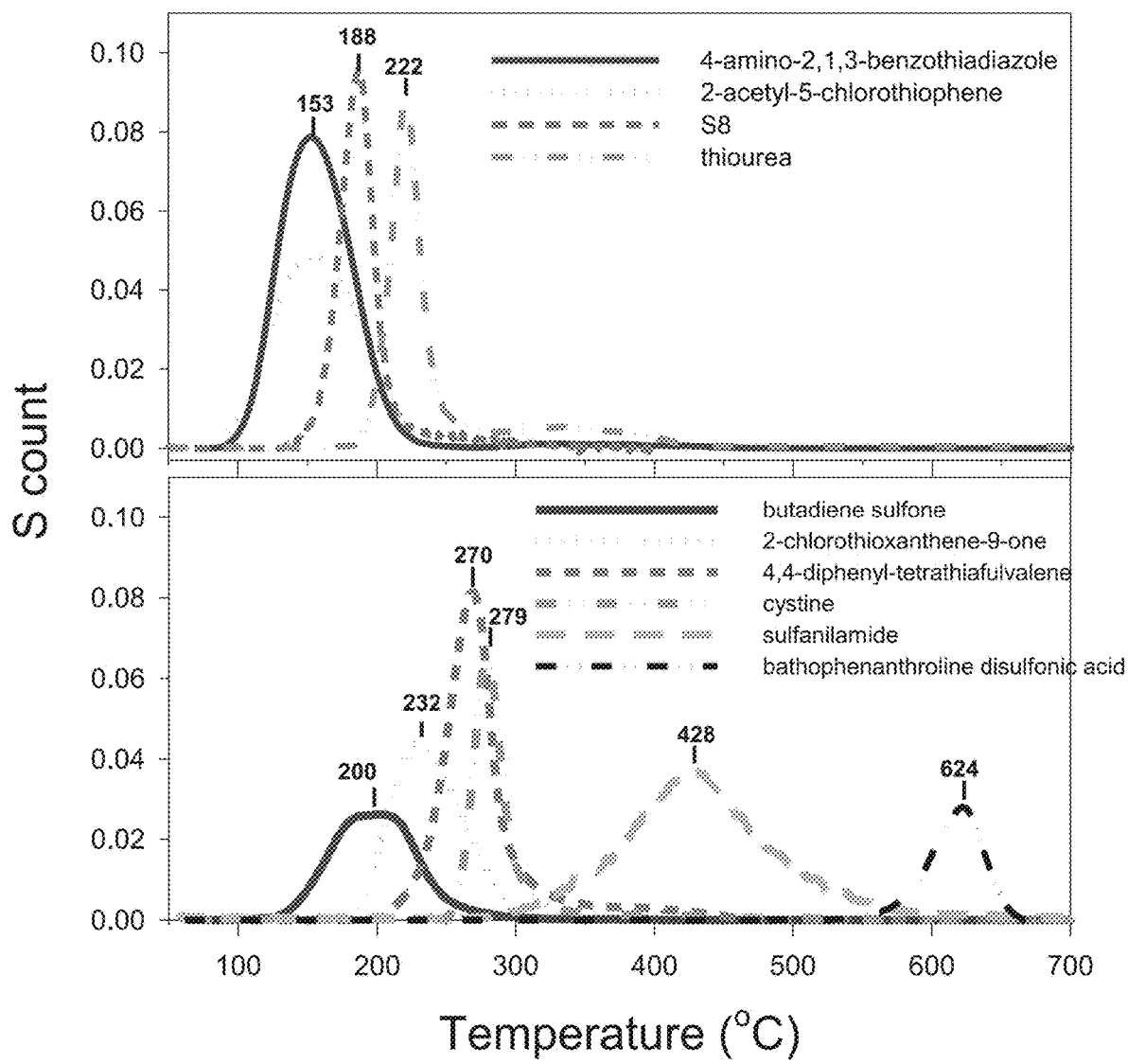
FIG. 1 depicts sulfur thermograms of the reference compounds with single and symmetrical peaks.

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

Generally, the current invention is a method of directly analyzing organic matter sulfur within environmental samples, in particular crude oil samples, using the MESTA technique. This thermochemical methodology is demonstrated herein in the analysis of organic sulfur and reduced inorganic sulfur in reference sulfur compounds, aerosols, soils, sediments, plants, foods, petroleum, and coal, with results indicating efficiency and efficacy of the methodology. The results indicate that the method is sensitive (<0.01 μg), convenient, and versatile (applicable to a wide range of solid, liquid, or mixed samples). The method also quantifies reduced inorganic sulfur species.

In certain embodiments, the current invention is a method of analyzing crude oil (e.g., for distillation ranges and their sulfur and nitrogen impurities) based on MESTA technology. The analysis can be performed rapidly (e.g., ~30 minutes) and at a fraction of the costs of conventional methodologies. The MESTA procedure can obtain the distillation ranges (e.g., ~7-15 boiling-point distillation ranges) and their sulfur and nitrogen impurities in each range within a single analysis; this is possible due to the MESTA thermograms of C, N, S, and H being quantitatively related to the distillation property (boiling points) of hydrocarbon, sulfur, and nitrogen compounds in a crude oil sample. Furthermore. MESTA is a continuous fractionation method, where the results of one analysis contain all-possible-fraction information, and it is a continuous thermal scanning technique, where the thermogram continuously scans in a temperature range from ambient to about 700° C. One analysis contains all possible distillation range information, which otherwise can only be obtained individually by many specified fixed range distillation procedures. There is no need to re-analyze a sample if one wants to know other options of fractionation. It produces no hazardous material in a laboratory and could be mobile for on-site analysis. After a specific sample handling procedure and kinetic effect correction function identification, the accuracy of this MESTA based method has been validated by comparison with results from the traditional boiling-point (10 ranges) distillation method. The results of the MESTA based method are highly agreeable with those of the traditional methods.

Study 1
Materials & Methods
Materials

Reference sulfur compounds of 4-amino-2,1,3-benzothiadiazole, 2-acety-5-chlorothiophene, elemental sulfur (S8), butadiene sulfone, thiourea, 2-chlorothioxanthen-9-one, 4,4-diphenyl-tetrathiafulvalene, cystine, sulfanilamide, bathophenathrolinedisulfonic acid, bis(diethyldithiocarbamato) dioxomolybdenum(VI), DL methionine sulfoxide, cysteine, dithiouracil, sodium thiosulfate, sulfanilic acid, sulfides, and bi-sulfides were obtained from SIGMA-ALDRICH.

Two crude oil samples were obtained from ONTA Inc.: an Appalachian Basin light, sweet (S<0.5%) paraffin base crude oil and a Venezuelan heavy, sour (S >0.5%) asphalt base crude oil. The Appalachian Basin light is used to produce gasoline and kerosene and high-quality diesel. The Venezuelan heavy sour crude oil has its sulfur mostly bonded to carbon. A synthetic crude oil sample was obtained courtesy of Dr. Clifford Louime.

MESTA Analysis

Samples were removed from cold storage and placed in a desiccator prior to weighing. CRM coal and crude oil samples were mixed with pre-baked talc (weight ratio 1:5) before MESTA analysis. Loss on ignition (600° C., 2 hrs.) was used to confirm the exact content of the crude oil in talc.

Details of the MESTA procedure can be found in previous work by the current inventors (Y. P. Hsieh, A novel multi-elemental scanning thermal analysis (MESTA) method for the identification and characterization of solid substances, J AOAC Int. 2007 January-February, 90(1): 54-59: Y. P. Hsieh et al., Analysis of black carbon in sediments and soils using multi-element scanning thermal analysis (MESTA), Organic Geochemistry 39 (2008) 1562-1571), which are incorporated herein by reference in their entireties. Briefly, the sample compartment furnace was programmed to heat from 40° C. to 800° C. at a constant heating rate (e.g., 50° C./min here) with a 40/60 volume mixture of extra-high purity $O_2$ and He gases as a carrier gas (i.e., oxygen content of the carrier gas was 40% in helium). The gas flow rates in the sample compartment and combustion furnace were 80 mL/min and 350 mL/min, respectively.

The selected heating rate and carrier gas composition of the MESTA minimize the artifact of charring organic carbon into the black carbon during the thermal analysis (Y. P. Hsieh et al., Analysis of black carbon in sediments and soils using multi-element scanning thermal analysis (MESTA), Organic Geochemistry 39 (2008) 1562-1571).

A comparison of MESTA thermograms between a reference compound and a sample or among samples is performed under the same heating rate of the MESTA procedure. In this study, a heating rate of 50° C./min was used-significantly higher than the 10° C./min rate used by many other thermal analytical methods. A higher heating rate produces more sensitive results for MESTA, though the deviation of the peak temperature may be greater as well.

The carrier gas carried the volatile from the sample during heating into a high-temperature (e.g., 1100° C. or 2012° C.) combustion furnace that is continuously fed by 100% extra-high purity oxygen. In the combustion compartment, the C, N, and S contents of the volatile were oxidized into their respective gaseous oxides ($CO_2$, $NO_2$, and $SO_2$) and quantified by their respective detectors ($CO_2$ IR analyzer, $NO_2$ chemiluminescent detector, and S02 chemiluminescent detector). A PC-based multi-channel digital data logger (NATIONAL INSTRUMENT 6034E, Austin, Tex.) was used to record the real-time sample temperature, $CO_2$ signals, $NO_2$ signals, and $SO_2$ signals simultaneously. Standard calibration curves of C, N. and S were obtained by mixtures of pure cystine and glucose standards. The temperature of the sample was calibrated using internal standards of elemental sulfur and silver sulfide ($Ag_2S$).

Unlike most TGA/IR/MASS systems, which often have condensation problems in the connection tubing between the sample furnace and GC/MASS detectors at temperatures exceeding 350° C. (662° F.), the MESTA sample compartment and the high-temperature combustion compartment are configured in a way that a positive temperature gradient is always maintained from the sample to the combustion compartment throughout the analysis. No condensation of the volatile or cross-contamination among samples could occur in the instrument because of this positive temperature gradient. This can be considered a "self-cleaning" process after each analysis, which ensures the sensitivity and reproducibility of the analysis, especially in the heavy crudes. The configuration of the sample compartment allows not only a controlled sample heating rate but also controlled sample atmosphere, which adds flexibility in MESTA.

Results

Reference Sulfur Compounds

According to the peak distribution of the sulfur thermogram, the reference sulfur compounds were classified into three categories: (1) single-peak. (2) multiple-peak, and (3) skewed-peak.

The single-peak category is represented by the compounds of 4-amino-2,1,3-benzothiadiazole, 2-acety-5-chlorothiophene, elemental sulfur (S8), butadiene sulfone, thiourea. 2-chlorothioxanthen-9-one, 4,4-diphenyl-tetrathiafulvalene, cystine, sulfanilamide, and bathophenathrolinedisulfonic acid in the order of ascending decomposition temperatures (FIG. 1). The thermograms of those sulfur compounds suggest that the sulfur in the compound decomposed at a certain temperature resulting in a single and symmetrical peak. There are overlapping decomposition temperatures for those compounds. For example, 4-amino-2,1,3-benzothiadiazole and 2-acety-5-chlorothiophene have sulfur peaks at 153° C. and thiourea and 2-chlorothioxanthen-9-one have decomposition peaks at 222° C. and 232° C., respectively. However, the peak height/half-height width (PH/HHW) ratios of those peaks, after normalization of peak heights (area under peaks), are quite distinguishable among these compounds. The PH/HHW ratio of 4-amino-2,1,3-benzothiadiazole and 2-acety-5-chlorothiophene are 4.9 and 2.2, respectively. Similarly, the PH/HHW ratio of thiourea and 2-chlorothioxanthen-9-one are 15 and 2.5, respectively. Differences in C. N, and S ratios of the compounds (FIG. 1), which are also determined by MESTA, provide extra criteria for identifying compounds with similar decomposition temperatures.

Figure 2:
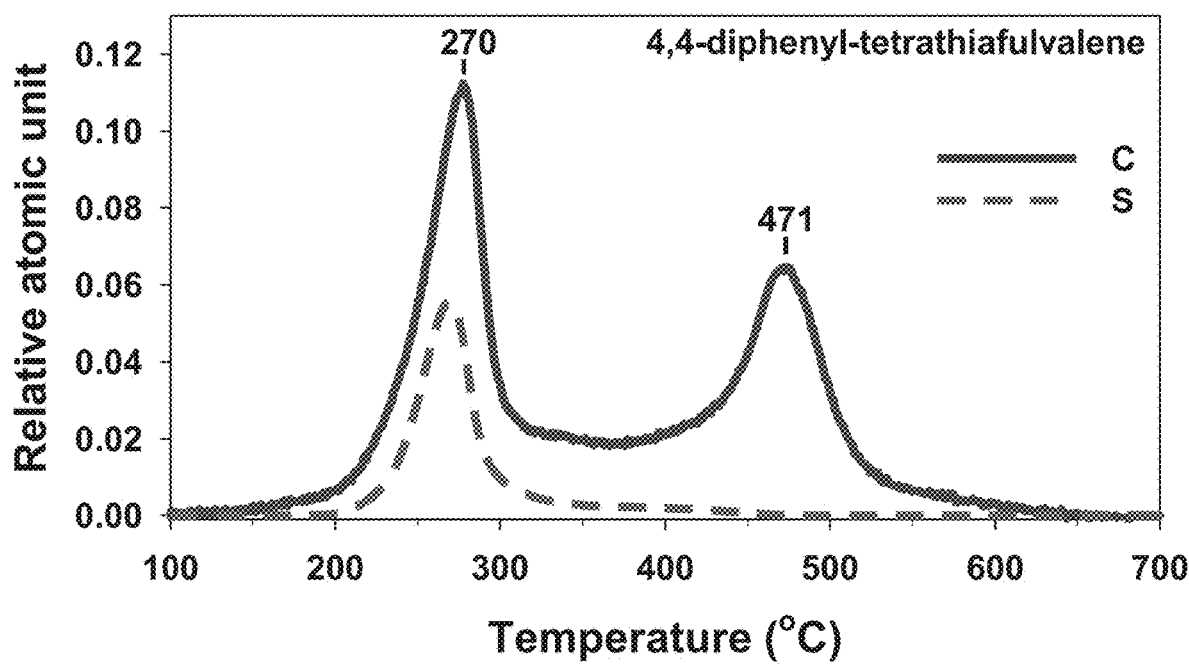
FIG. 2 depicts the carbon and sulfur thermograms of 4,4-diphenyl-tetrathiafulvalene. There are two carbon peaks: the 270° C. peak has the companion sulfur peak, whereas the 471° C. peak has none. The 471° C. peak is the non-sulfur carbon skeleton of the compound after the 270° C. thermal decomposition.

In some cases, characteristic carbon thermograms can also provide clues for identifying compounds. For example, 4,4-diphenyl-tetrathiafulvalene has a single sulfur peak at 270° C. There are, however, two carbon peaks for this compound in MESTA: one corresponds to the 270° C. sulfur peak, and the other does not correspond to any sulfur at 471° C., representing the "de-sulfured" skeleton of the compound (FIG. 2).

Figure 3:
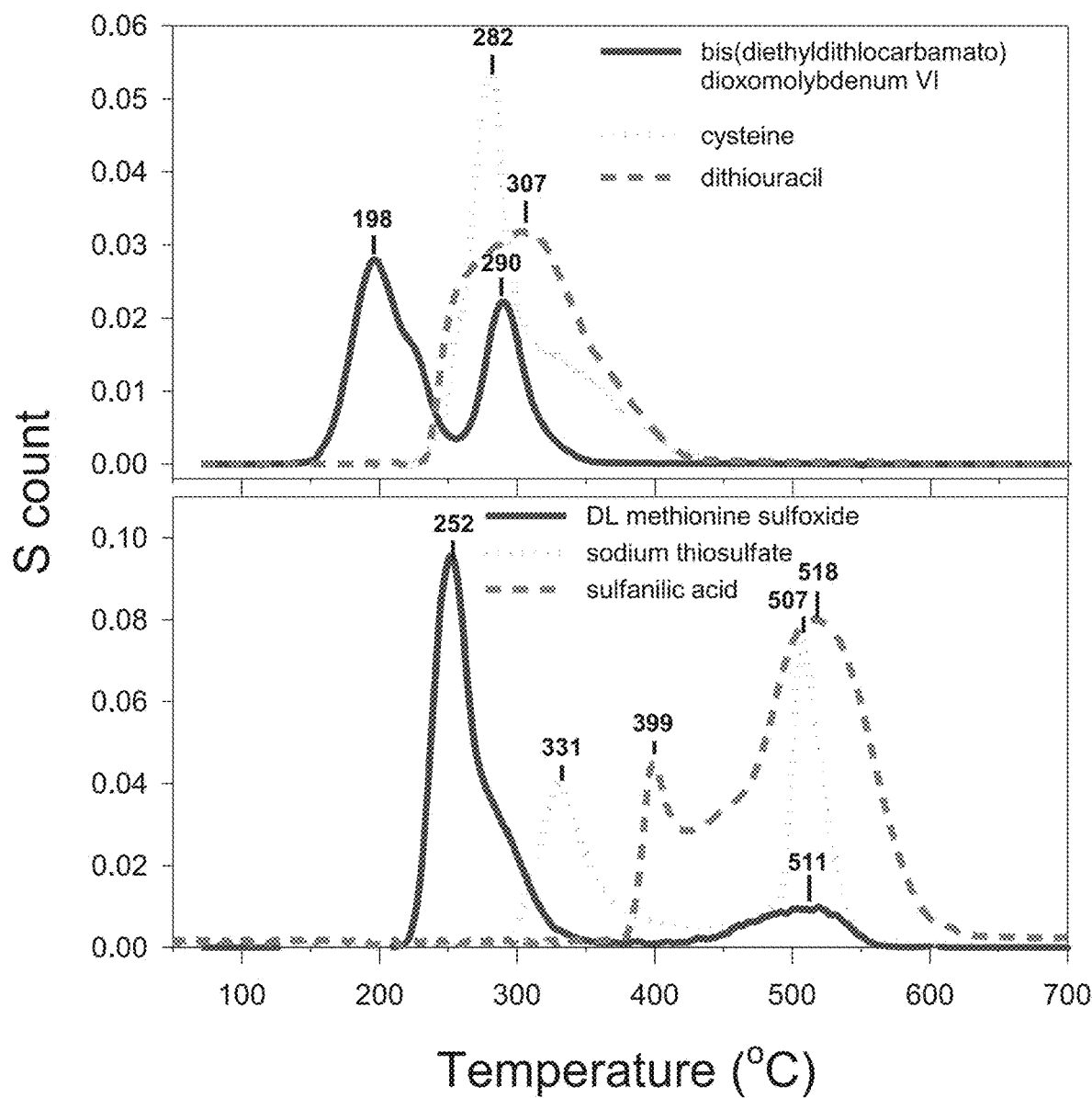
FIG. 3 depicts the sulfur thermograms of the reference compounds with multiple sulfur peaks.
Figure 4:
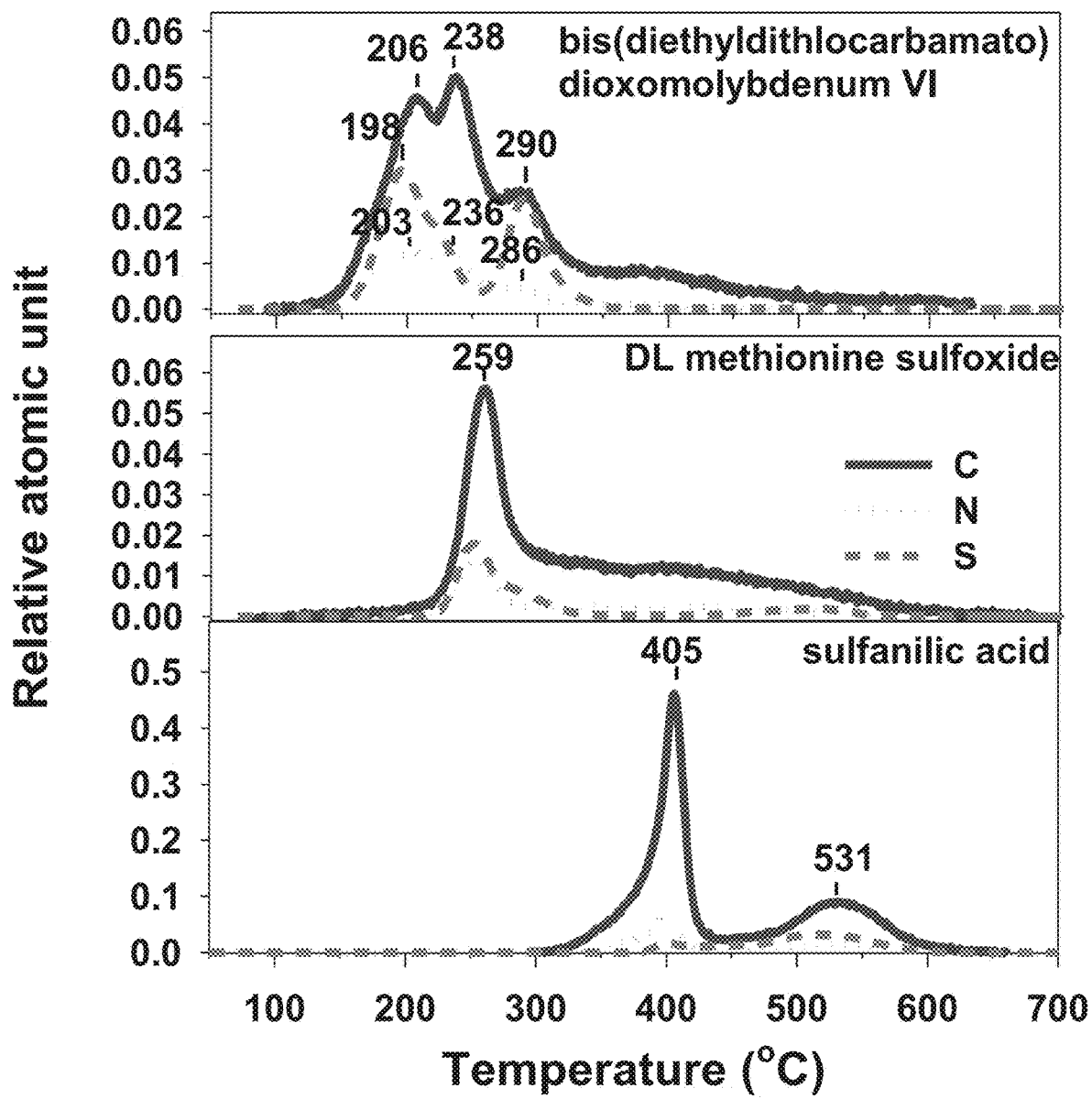
FIG. 4 depicts MESTA thermograms, showing the relative carbon, nitrogen, and sulfur atomic ratios of reference compounds with multiple sulfur peaks.

The multi-peak category is represented by the compounds of bis(diethyldithiocarbamato) dioxomolybdenum(VI), DL methionine sulfoxide, cysteine, dithiouracil, sodium thiosulfate ($Na_2S_2O_3$) and sulfanilic acid (FIG. 3). Apparently, the functional sulfur group in this category goes through incongruent thermal decomposition. Part of the sulfur was directly oxidized or vaporized. The rest of the sulfur, however, reacted with other functional groups of the molecule, such as the amides, and decomposed at higher temperatures. Obvious examples of this category are bis(diethyldithiocarbamato) dioxomolybdenum(VI), sulfanilic acid, DL methionine sulfoxide, and sodium thiosulfate. Furthermore, the companying C and N thermograms give more information pertaining to the plausible interaction between S and N functional groups and more criteria to differentiate those sulfur compounds (FIG. 4).

Figure 5:
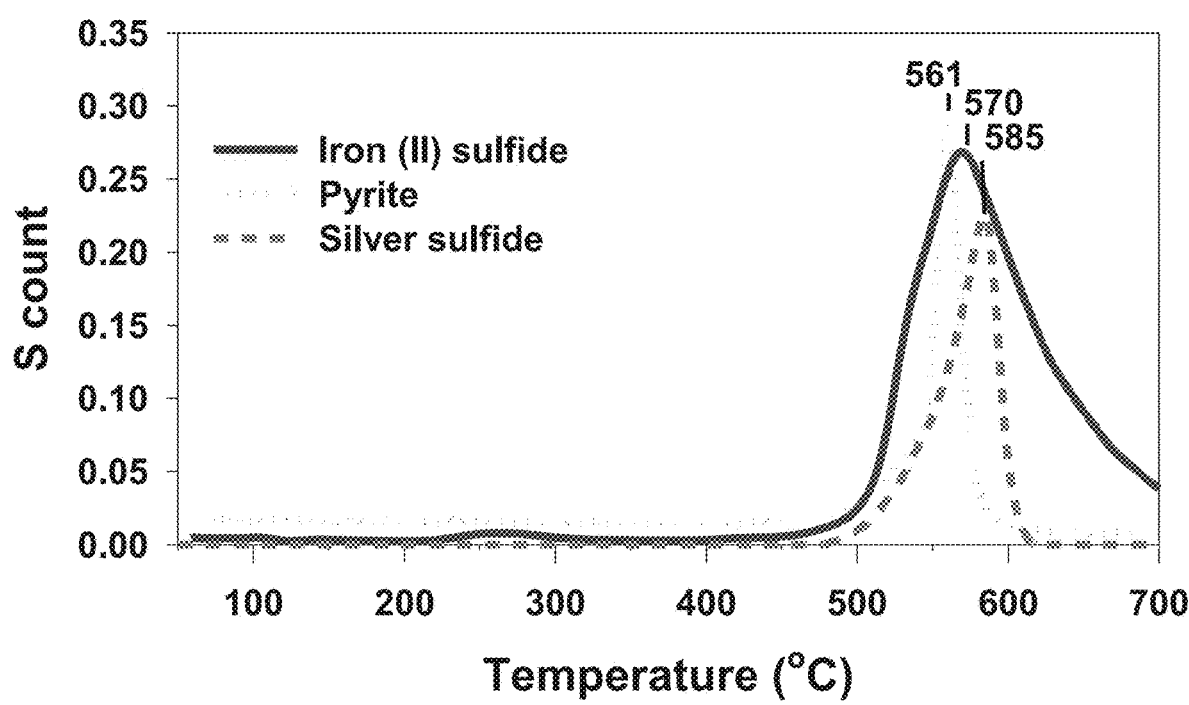
FIG. 5 depicts the sulfur thermograms of the reference compounds with skewed sulfur peaks.

The skewed-peak category (FIG. 5) is represented by the reduced inorganic sulfur of sulfides and bi-sulfide ($Fe(II)S_2$). Sulfides and bi-sulfides all have similar thermal decomposition/oxidation temperatures that peaked between 561-585° C. Pure and freshly made sulfides and bi-sulfides have sharper peaks (PH/HHW>9). They, however, are subject to oxidation in the air during storage, depending on the humidity. Partially oxidized sulfides and bi-sulfides may have peaks skewed towards lower temperatures in the form of sulfite. Commercial iron sulfide has a characteristic asymmetric peak skewed towards higher temperatures (FIG. 5) as well.

Sulfate was intentionally excluded from the analysis because it created cross-contamination problem in the MESTA device. Sulfate salts by itself, even in the form of ammonium sulfate, can be easily excluded in the MESTA because they vaporized negligible below 800° C. In the case of ammonium sulfate, when nitrogen was observed at peaks of 234° C. and 289° C., there was no simultaneously evolved sulfur. Trace of sulfur (<2%) started to appear around 700° C., indicating that the majority of the dissociated sulfate likely re-deposited in the sample compartment below 700° C., where cations such as Na, K, Mg or Ca are abundant.

If a portion of sulfide is oxidized to sulfate, the decomposition temperature of that portion is drastically increased to beyond 850° C., which is not included herein. It was observed that repeatedly analyzing sulfate-containing samples beyond 850° C. would cause cross-contamination of samples because vaporized sulfates at high temperatures may re-deposit in the corner of the sample chamber where the temperature is slightly lower. The re-deposited sulfate becomes very difficult to clean afterward. Repeated analysis of sulfate at high temperatures beyond 850° C., therefore, could compromise the sensitivity of MESTA. For this reason, heating the sample beyond 800° C. was avoided, and sulfate may be excluded from the MESTA procedure. The shape of a sulfide peak can indicate the purity of the compound and the state of its partial oxidation.

Additionally, organosulfur in an unwashed sample is considered an artifact of MESTA. Any sample that may contain sulfuric acid, therefore, should be washed substantially free of sulfuric acid before MESTA to ensure that no organosulfur is created in the MESTA process.

Petroleum and Coal

Figure 6:
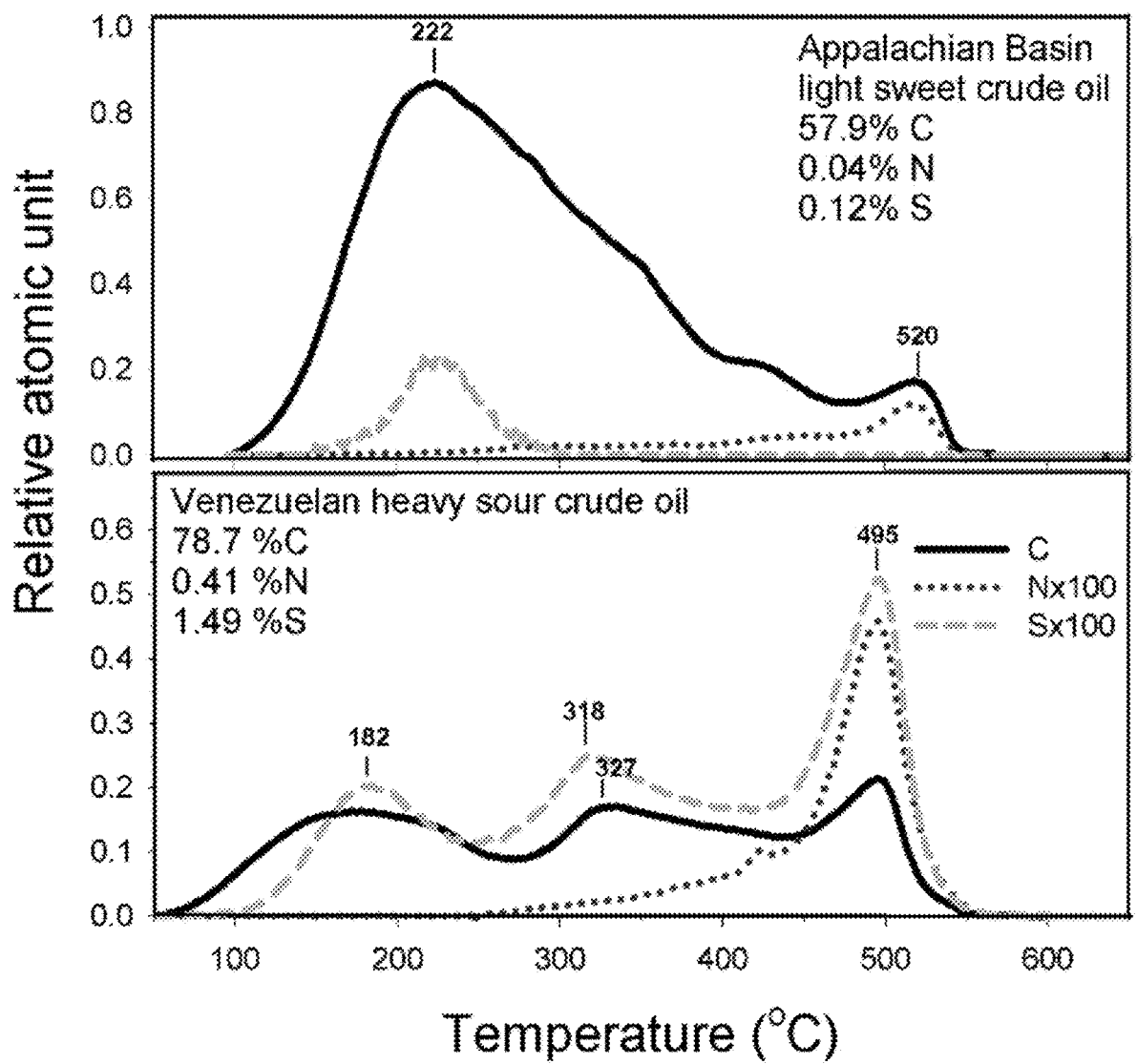
FIG. 6 depicts relative carbon, nitrogen, and sulfur atomic ratios of crude oil.

FIG. 6 presents the thermograms of the petroleum samples. The Venezuelan heavy sour crude was found to have a much high sulfur content than that of the Appalachian Basin light sweet crude. Not only is the quantity 12 times higher, but the quality of sulfur in the Venezuelan heavy sour crude was also quite different from that of the Appalachian Basin light sweet crude. The sulfur peak in the Appalachian Basin light sweet crude was low-temperature (222° C.) and symmetrical, indicating that it is relatively simple in composition. The sulfur peaks in the Venezuelan heavy sour crude sprayed from 182° C.-495° C., indicating a much broader and more complicated spectrum of compounds. The synthetic crude had non-detectable sulfur.

Figure 7:
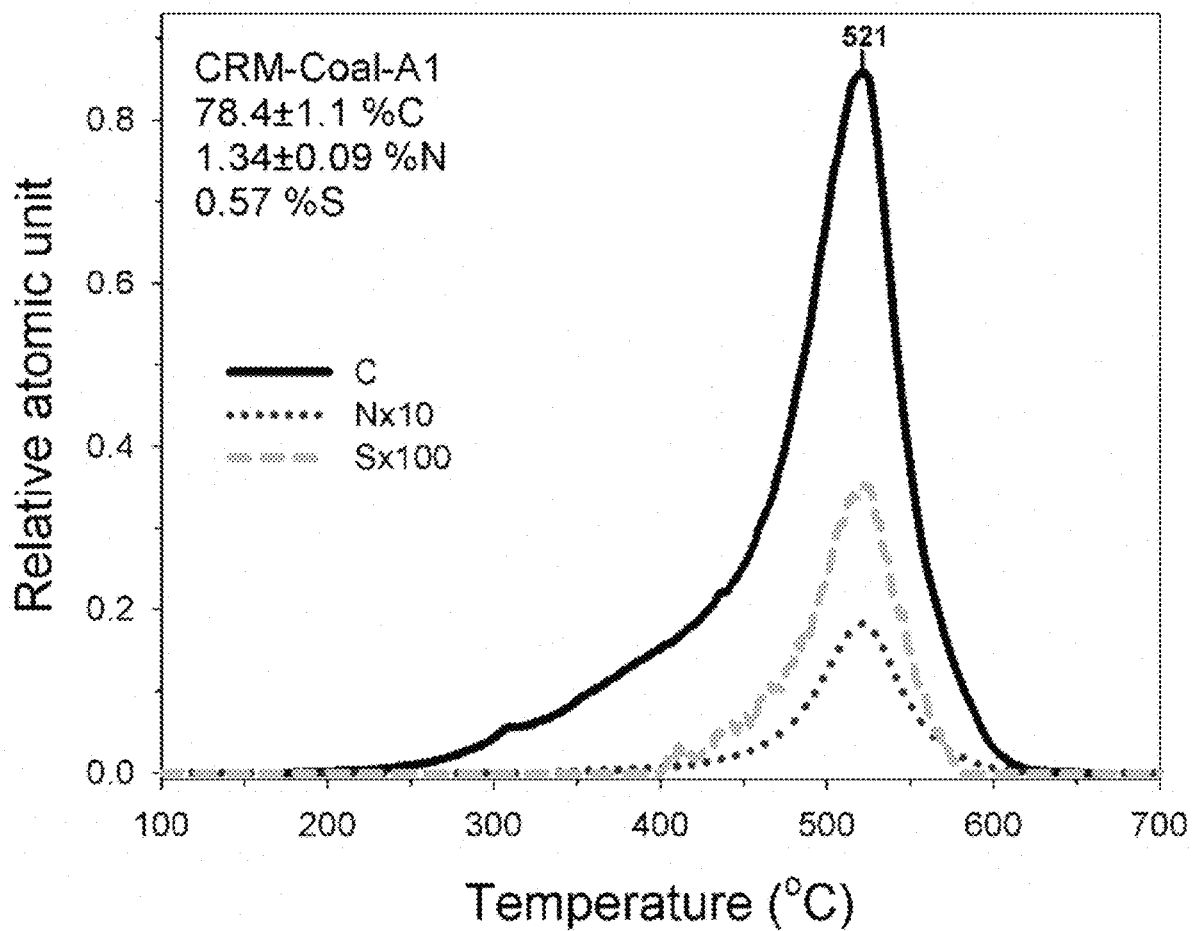
FIG. 7 depicts relative carbon, nitrogen, and sulfur atomic ratios of a coal reference material.

The thermogram of CRM coal is presented in FIG. 7. The sulfur peak appears at 521° C. which synchronizes with carbon and nitrogen peaks. The sulfur is organic, most likely in the form of the products of the reactions between sulfides and organic matter in the sediments before they were buried in the coal formation.

In light of the foregoing results (see also FIG. 8 to view peak information, including compound, chemical formula, molecular weight, and chemical structure), the current study demonstrates that MESTA can determine organic sulfur directly in heterogeneous and complex environmental samples such as soils, sediments, aerosols, petroleum, and coals. The MESTA sulfur analysis includes the entire spectrum of organic sulfur and reduced inorganic sulfur species, such as sulfides and bisulfides. MESTA is sensitive (detection limit <0.01 µg), convenient (no pretreatment required), and versatile (can handle solid, liquid, and mixed samples). It is suitable for the routine analysis of large amounts of environmental samples. Any sample that contains sulfuric acid should be washed with water to get rid of artifact organosulfur that may be created by the reaction of sulfuric acid and organic matter during the MESTA process.

Study 2

Methods

Sample Preparation

Crude oil contains hydrocarbons with a wide range of boiling points. The temperature range of the current version of MESTA is between 38.2° C. (or 10° F.) and 760CF (1400° F.). The sample chamber can be chilled to 0° C. (32° F.) to minimize the loss of very volatile hydrocarbons. Alternatively, the loss of very volatile hydrocarbons with boiling points are below 38.2° C. can be estimated before the MESTA procedure starts. A subsampling scheme can also be designed that can well represent the bulk sample because a MESTA sample size is at the mg level. To overcome the sampling problem, an exemplary strategy can be to identify a proper chemically/thermally inert material, such as talc, to serve as a mixing matrix that can absorb and distribute the oil uniformly for MESTA.

Adjustable Parameters—Carrier Gas Composition and Heating Rate of MESTA

The parameters of MESTA (mainly heating rate and the oxygen composition of the carrier gas) can be adjusted to optimize the performance of a particular application. For example, the application of MESTA in the analysis of black carbon in the environmental samples requires enhanced oxygen content in the carrier gas and slower heating rate of the sample to minimize the secondary black carbon formation (an artifact) during the analytical process. For crude oil analysis, MESTA can be run under an anoxic atmosphere (zero oxygen carrier gas) in the sample compartment to simulate the boiling-point distillation process with effective results. The bulk total C, N, and S contents of crude oil analyzed in a 33% oxygen atmosphere can be used, resulting in complete decomposition of the crude oil except for the ashes. Accordingly, the residual of crude oil beyond 80(PC (1472° F.) can be estimated.

A heating rat should also be selected and limited to reduce the "skewness" of the MESTA thermograms. A faster sample heating rate not only saves analytical time but also increases the sensitivity of the analysis. However, a faster scanning rate also increases the kinetic effect (i.e., deviation of the apparent boiling point from the true equilibrium boiling point) of MESTA. An optimal scanning (heating) rate of MESTA on crude oil analysis should be selected, where the heating rate both minimizes the kinetic effect and allows high sensitivity and speed of MESTA.

Results

The use of the MESTA technique resulted in the simultaneous quantitative C, N, S, and H thermograms of the sample, which are quantitatively related to the distillation property (boiling points) of the hydrocarbon, sulfur and nitrogen compounds of crude oil.

Figure 9:
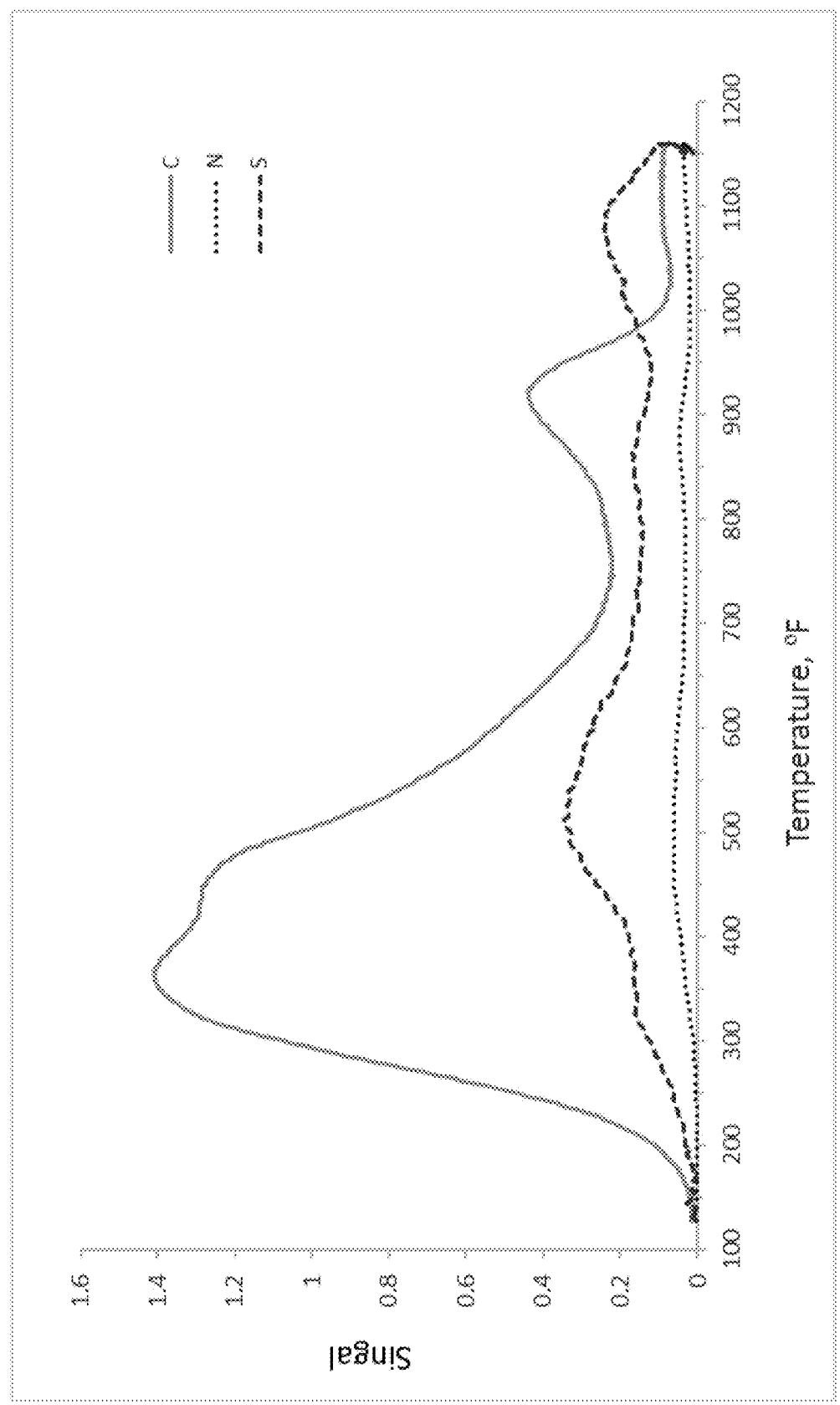
FIG. 9 depicts MESTA thermograms of C, N, and S of an SGS crude oil sample DP-15. The multiple-peak thermograms indicate that the sample was a mixture of materials with various boiling-point distillation ranges.

FIG. 9 shows the MESTA C, S, and N thermograms of a crude oil sample (DP-15 provided by SGS of Houston, Tex.). The multiple-peak thermograms indicate that it has multiple boiling-point ranges in the sample.

Figure 10:
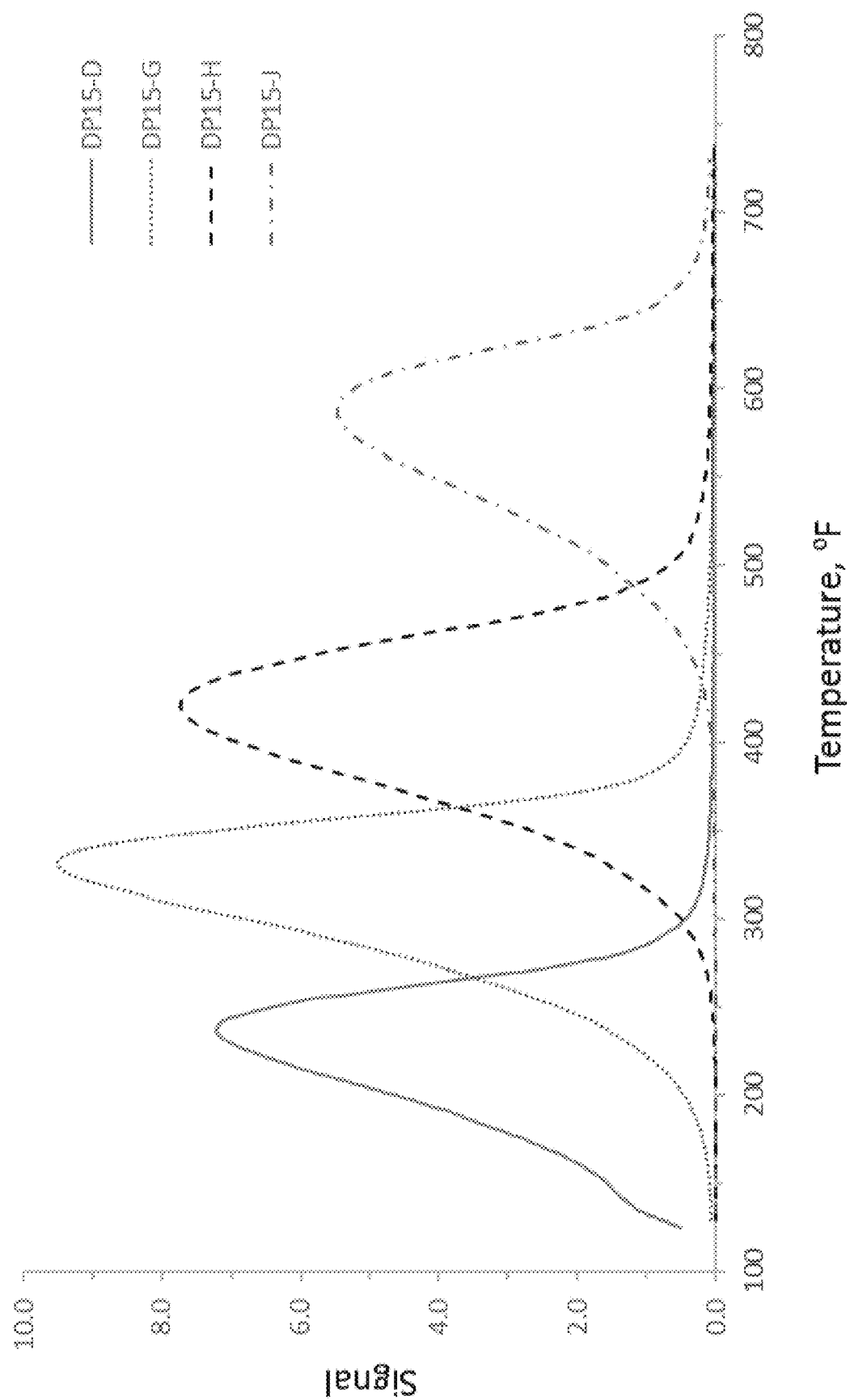
FIG. 10 depicts MESTA carbon thermograms of four distillation ranges of the SGS crude oil sample DP-15: D (450-500° F.), G (550-600° F.), H (650-800° F.) and J (900-1016° F.). The single-peak MESTA thermograms of those ranges confirm they were single boiling-point distillation ranges, and MESTA can separate them with their respective range temperatures.

FIG. 10 shows the MESTA carbon thermograms of the four boiling-point distillates, respectively, of the DP-15 crude oil sample obtained by the standard boiling-point distillation method (performed by SGS Laboratory). The four single-peak carbon thermograms with separated four temperature ranges indicate that they are all single boiling-point distillates. The peaks in FIG. 10 are not truly symmetrical but skewed slightly toward the direction of higher temperatures. This is because the MESTA is a kinetic method, and the degree of skewness is related to the heating rate of the sample.

Figure 11:
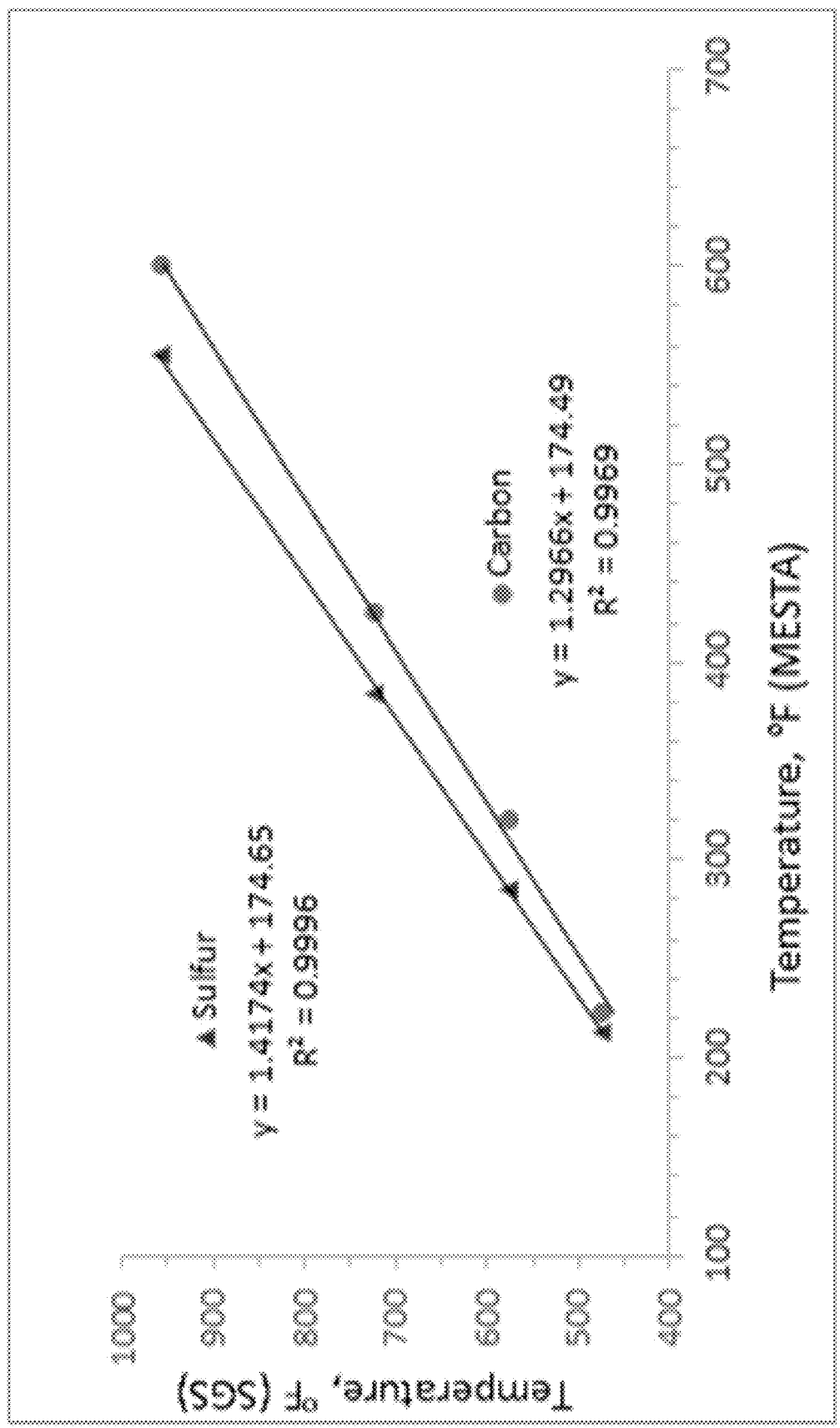
FIG. 11 depicts kinetic-effect correlation functions between the temperatures of the MESTA method and those of the boiling-point distillation method for carbon and sulfur, respectively. The kinetic-effect correction factors are linear for carbon and sulfur, and the correlations are highly significant.
Figure 12A:
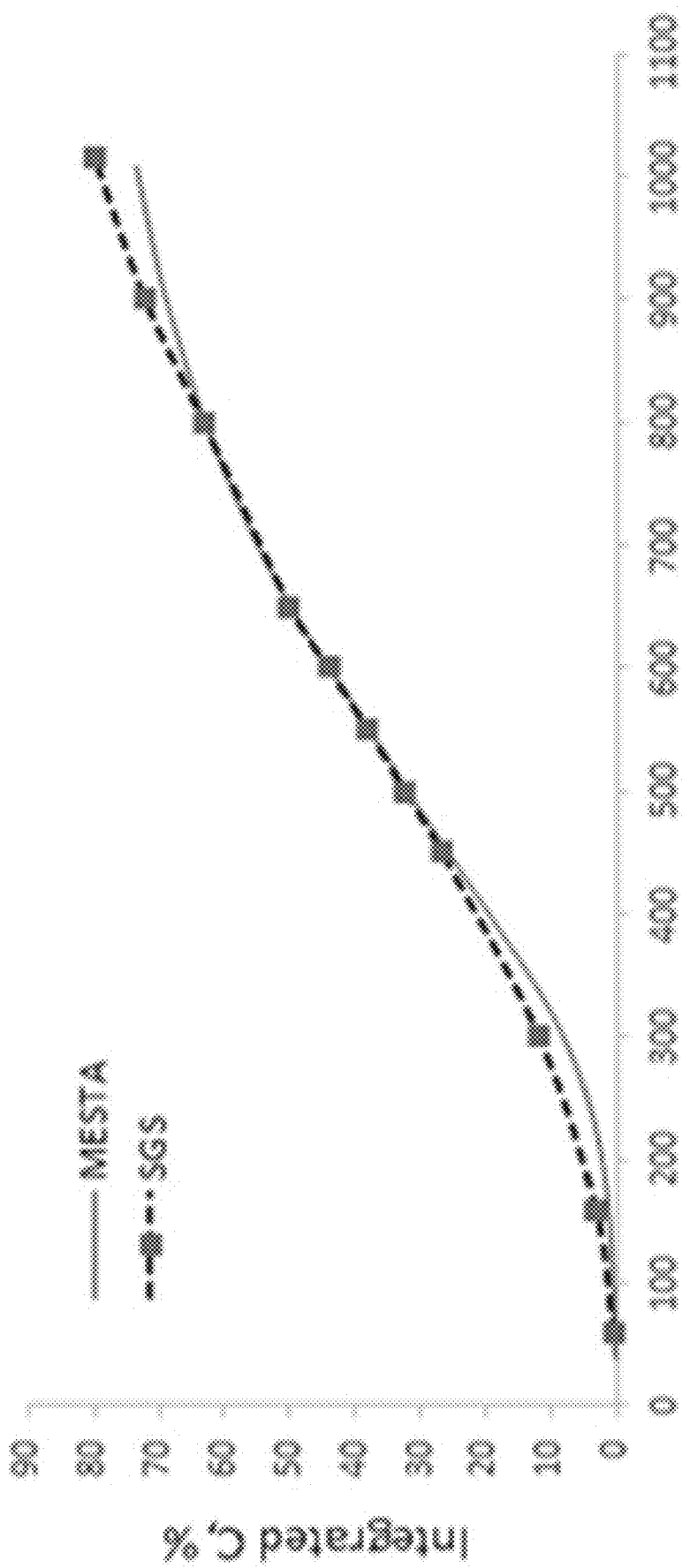
FIG. 12A is a graphical illustration comparing the cumulative weight percent of hydrocarbon of the crude oil sample (DP-15) obtained by the SGS distillation and sulfurnitrogen analyses (dashed lines) and by the MESTA based method after correction of the kinetic effect (solid lines).
Figure 12B:
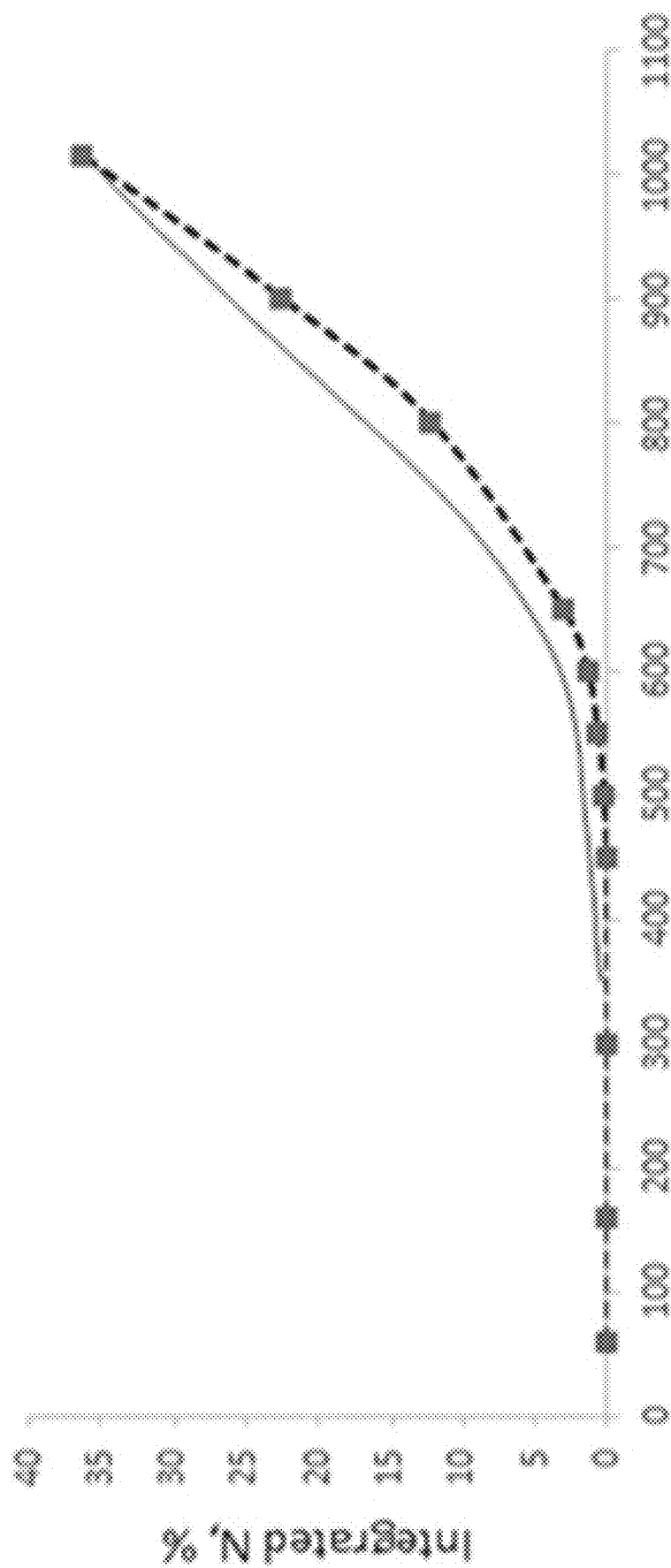
FIG. 12B is a graphical illustration comparing the cumulative weight percent of nitrogen compounds of the crude oil sample (DP-15) obtained by the SGS distillation and sulfur/nitrogen analyses (dashed lines) and by the MESTA based method after correction of the kinetic effect (solid lines).
Figure 12C:
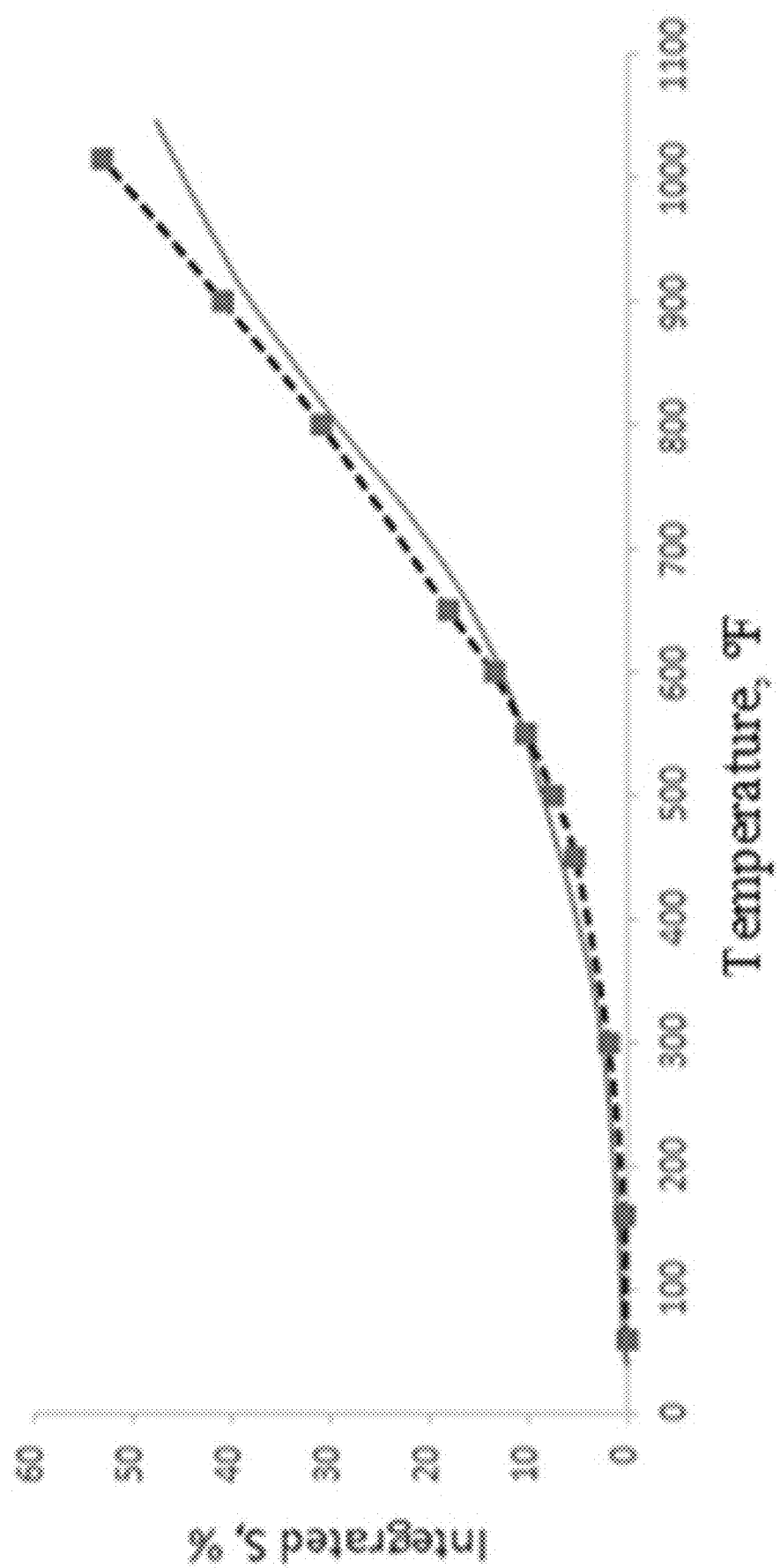
FIG. 12C is a graphical illustration comparing the cumulative weight percent of sulfur compounds of the crude oil sample (DP-15) obtained by the SGS distillation and sulfur/nitrogen analyses (dashed lines) and by the MESTA based method after correction of the kinetic effect (solid lines).

To compare the MESTA temperature to that of the batch-equilibrium distillation method, a kinetic effect correction function should be identified for the method. This kinetic effect correction function (FIG. 11) was identified and applied to the analysis of DP-15. The results, after the kinetic effect correction of the MESTA-based method, is highly agreeable with those of the traditional distillation methods (FIGS. 12A-12C), not only in the hydrocarbon fractions but also in their sulfur and nitrogen impurities.

The foregoing results illustrate that the current MESTA-based method can obtain the same quantitative information of the detailed crude oil analysis, as the conventional distillation method, plus the sulfur/nitrogen impurities information in each range by a single analysis. Software applications within MESTA allow the thermograms to be expressed quantitatively in many convenient forms, such as their relative atomic ratios, the cumulative percentage of distillates, or other quantitative expressions of the results.

Glossary of Claim Terms

About: This term is used herein to mean approximately or nearly and in the context of a numerical value or range set forth means ±15% of the numerical. In an embodiment, the term "about" can include traditional rounding according to significant figures of the numerical value. In addition, the phrase "about 'x' to 'y'" includes "about 'x' to about 'y'." The term "approximate" can be used interchangeably with the term "about."

Distillation properties: This term is used herein to refer to the features of a multi-element compound pertaining to the separation of compounds or elements from each other through heating. The boiling point of a compound is an example of one of its distillation properties.

Internal standards of elemental sulfur and silver sulfide: This term is used herein to refer to the two-point temperature calibration of the sample furnace.

Multi-element scanning thermal analysis: This term is used herein to refer to the continual analysis of elemental properties of a specific sample across a range of temperatures, i.e., changes in the properties during temperature change.

Overlapping decomposition temperature: This term is used herein to refer to a temperature at which multiple elements or compounds within a sample decompose during heating thereof. The overlap may pose difficulty in accurately identifying compounds and elements within the sample. This difficulty may be overcome by normalizing the area under the peaks on the thermogram/graphical illustration, which further differentiates the compounds/elements.

Species: This term is used herein to refer to an elemental component of a multi-element sample to be analyzed, where the component may exist on its own or within a larger compound.

Thermogram: This term is used herein to refer to a graphical illustration and/or temperature map generated during the thermal analysis of a sample.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of analyzing a sample using multi-element scanning thermal analysis, the method comprising the steps of:
    heating the sample within a sample compartment furnace;
    disposing a carrier gas through the sample compartment furnace to a combustion furnace, thereby carrying volatile from the sample compartment furnace during heating of the sample to the combustion furnace, such that one or more elements within the sample are oxidized;
    quantifying the one or more elements using a chemiluminescent detector;
    utilizing a multi-channel data logger to record real-time signals from the chemiluminescent detector and real-time sample temperature;
    displaying peak information within a thermogram indicating the presence of the one or more elements within the sample, wherein the thermogram is quantitatively related to a distillation property of the one of more elements; and
    continuously scanning the sample using the multi-channel data logger in a temperature range from ambient to about 700° C.,
    whereby multi-element scanning thermal analysis determines the one or more elements within the sample.

2. The method of claim 1, wherein the method further comprising continuously scanning the sample using the multi-channel data logger, wherein the thermogram obtained contains all possible distillation range information, whereby multi-element scanning thermal analysis simultaneously determines the one or more elements and distillation ranges within the sample.

3. The method of claim 2, wherein the one or more elements in the sample includes a nitrogen species and a sulfur species, wherein the nitrogen species in the sample is determined simultaneously with the distillation ranges and the sulfur species in the sample by performing the multi-element scanning thermal analysis on the sample.

4. The method of claim 2, wherein the one or more elements includes a sulfur species, a carbon species, a nitrogen species, and a hydrogen species, wherein the sulfur species, the carbon species, the nitrogen species, and the hydrogen species correspond to distillation properties of sulfur compounds, hydrocarbon compounds, and nitrogen compounds in the sample.

5. The method of claim 4, wherein differences in ratios of the carbon species, the nitrogen species, the sulfur species, and the hydrogen species within the sample are determined based on the thermogram.

6. The method of claim 1, wherein the multi-element scanning thermal analysis includes a constant heating rate with flow of a carrier gas.

7. The method of claim 1, wherein the carrier gas is an approximate 40/60 volume mixture of oxygen and helium, whereby the mixture minimizes an artifact of charring organic carbon into black carbon during the multi-element scanning thermal analysis.

8. The method of claim 1, wherein the flow rate of the carrier gas in a sample compartment furnace and in a combustion furnace is about 80 mL/min and about 350 mL/min, respectively.

9. The method of claim 1, further comprising calibrating a temperature of the sample using elemental sulfur and silver sulfide internal standards to ensure proper temperature readings during the multi-element scanning thermal analysis.

10. The method of claim 1, further comprising washing the sample substantially free of sulfuric acid prior to performing the multi-element scanning thermal analysis to ensure that no organosulfur is created during the multi-element scanning thermal analysis.

11. A method of analyzing a sample using multi-element scanning thermal analysis, the method comprising the steps of:
    heating the sample within a sample compartment furnace;
    disposing a carrier gas through the sample compartment furnace to a combustion furnace, thereby carrying volatile from the sample compartment furnace during heating of the sample to the combustion furnace, such that one or more elements within the sample are oxidized;
    quantifying the one or more elements using a chemiluminescent detector;
    utilizing a multi-channel data logger to record real-time signals from the chemiluminescent detector and real-time sample temperature;
    displaying peak information within a thermogram indicating the presence of the one or more elements within the sample, wherein the thermogram is quantitatively related to a distillation property of the one of more elements; and
    continuously scanning the sample using the multi-channel data logger in a temperature range from ambient to about 700° C., where the thermogram obtained contains all possible distillation range information,
    whereby multi-element scanning thermal analysis simultaneously determines the one or more elements and distillation ranges within the sample.

12. The method of claim 11, wherein the one or more elements in the sample includes a sulfur species, wherein the sulfur species include organic sulfur and reduced inorganic sulfur.

13. The method of claim 12, wherein the one or more elements in the sample includes a nitrogen species, wherein the nitrogen species in the sample is determined simultaneously with the distillation ranges and the sulfur species in the sample by performing the multi-element scanning thermal analysis on the sample.

14. The method of claim 11, wherein the one or more elements includes a sulfur species, a carbon species, a nitrogen species, and a hydrogen species, wherein the sulfur species, the carbon species, the nitrogen species, and the hydrogen species correspond to distillation properties of sulfur compounds, hydrocarbon compounds, and nitrogen compounds in the sample.

15. The method of claim 11, wherein the multi-element scanning thermal analysis includes continuous scanning in a temperature range from about 40° C. to about 800° C. within a programmed sample compartment furnace.

16. The method of claim 11, wherein the one or more elements includes a sulfur species, a carbon species, a nitrogen species, and a hydrogen species, the carrier gas carries volatile from the sample during heating into the combustion furnace that is fed by oxygen, thereby oxidizing the carbon species into carbon dioxide, the nitrogen species into nitrogen dioxide, the sulfur species into sulfur dioxide, and the hydrogen species into water.

17. The method of claim 14, further comprising the steps of:

generating calibration curves of the carbon species, the nitrogen species, and the sulfur species based on known standards of mixtures of pure cystine and glucose; and distinguishing between compounds having overlapping decomposition temperatures by normalizing the area under the peaks in the calibration curves, thus quantifying the carbon species, the nitrogen species, the hydrogen species, and the sulfur species.

18. The method of claim 11, further comprising calibrating a temperature of the sample using elemental sulfur and silver sulfide internal standards to ensure proper temperature readings during the multi-element scanning thermal analysis.

19. The method of claim 11, further comprising washing the sample substantially free of sulfuric acid prior to performing the multi-element scanning thermal analysis to ensure that no organosulfur is created during the multi-element scanning thermal analysis.

* * * * *